(12) United States Patent
Hunt

(10) Patent No.: US 11,717,643 B2
(45) Date of Patent: Aug. 8, 2023

(54) DEVICE FOR MIDSTREAM SAMPLE COLLECTION FROM A CATHETERIZED SUBJECT AND METHOD AND SYSTEMS FOR USE THEREOF

(71) Applicant: Stephen J. Hunt, Sandy, UT (US)

(72) Inventor: Stephen J. Hunt, Sandy, UT (US)

( * ) Notice: Subject to any disclaimer, the term of this patent is extended or adjusted under 35 U.S.C. 154(b) by 291 days.

(21) Appl. No.: 17/129,623

(22) Filed: Dec. 21, 2020

(65) Prior Publication Data

US 2021/0322720 A1 Oct. 21, 2021

Related U.S. Application Data

(60) Provisional application No. 63/089,510, filed on Oct. 8, 2020, provisional application No. 63/010,491, filed on Apr. 15, 2020.

(51) Int. Cl.
*A61M 25/00* (2006.01)
*A61M 39/22* (2006.01)
*A61F 5/455* (2006.01)

(52) U.S. Cl.
CPC ......... *A61M 25/0017* (2013.01); *A61F 5/455* (2013.01); *A61M 39/22* (2013.01); *A61M 2210/1092* (2013.01)

(58) Field of Classification Search
CPC ... A61M 25/0017; A61M 39/22; A61F 5/455; A61B 10/007
See application file for complete search history.

(56) References Cited

U.S. PATENT DOCUMENTS

| | | | | |
|---|---|---|---|---|
| 4,423,741 A | * | 1/1984 | Levy | A61B 10/007 137/625.68 |
| 5,616,138 A | * | 4/1997 | Propp | A61F 5/451 604/350 |
| 5,919,146 A | * | 7/1999 | Propp | A61B 5/208 604/326 |
| 2016/0030656 A1 | * | 2/2016 | Eikelmann | A61M 1/3643 137/15.05 |
| 2019/0209827 A1 | * | 7/2019 | Ziv | A61M 39/223 |

* cited by examiner

*Primary Examiner* — Sarah Al Hashimi
*Assistant Examiner* — Nhu Q. Tran
(74) *Attorney, Agent, or Firm* — Dorsey & Whitney LLP

(57) ABSTRACT

Disclosed herein are devices and methods for collecting samples of bodily fluid that may be substantially free of contamination, even where an initial amount of contamination may be present in a collection device, such as a urethral catheter. In the disclosed device and methods, the sample may be collected mid-stream, after an initial amount of fluid has flushed away the initial contamination. The disclosed devices may include a diverter device comprising a fluid control valve that may manually be moved between a first position and a second position that, respectively, direct fluid to two different channels and/or receptacles.

21 Claims, 7 Drawing Sheets

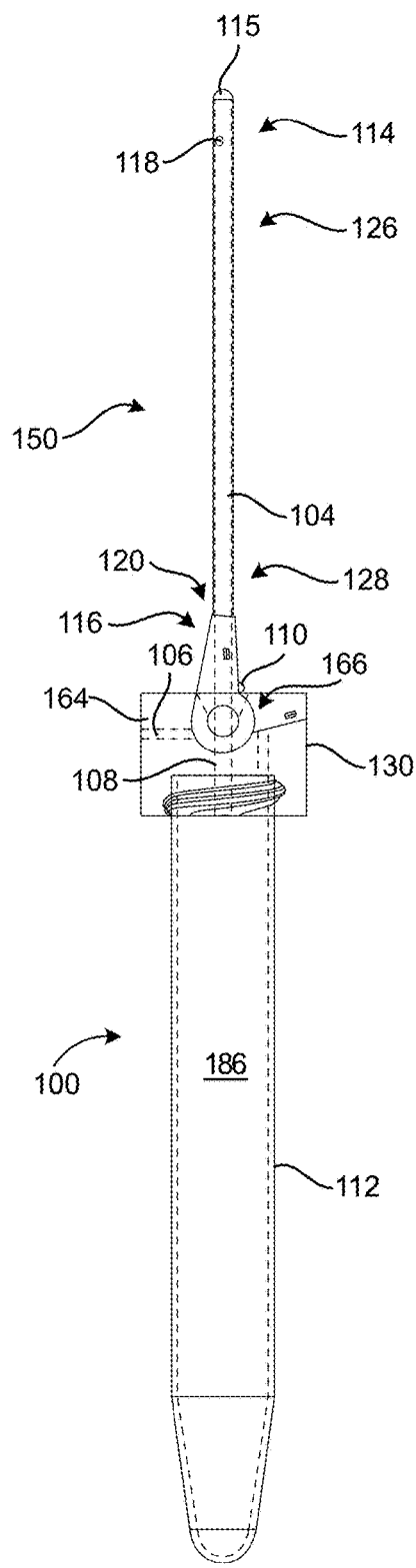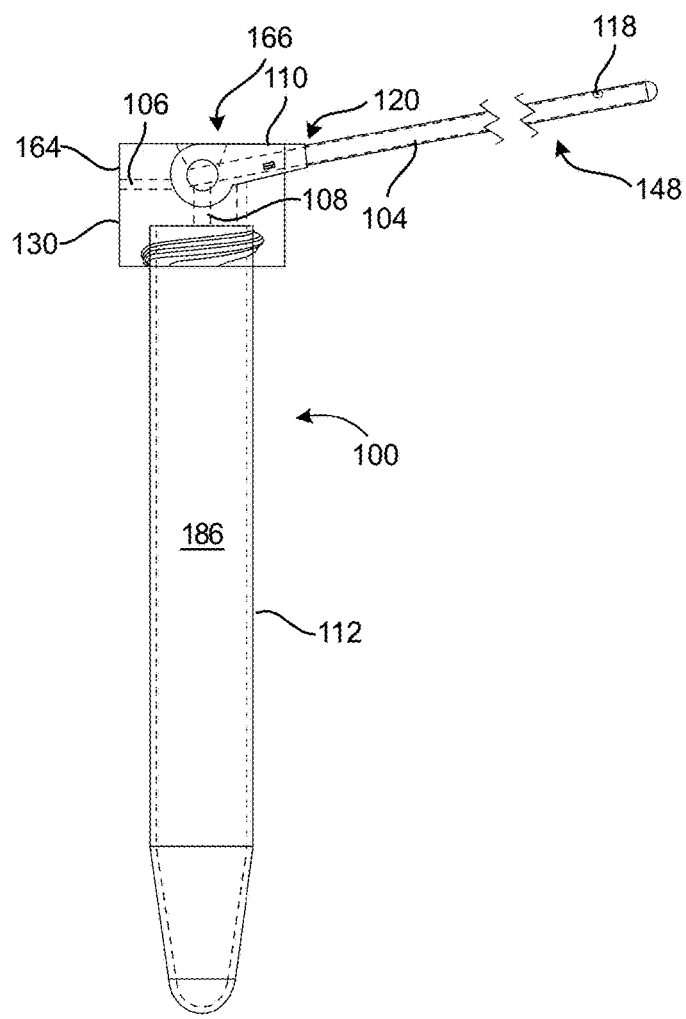
FIG. 1A
FIG. 1B

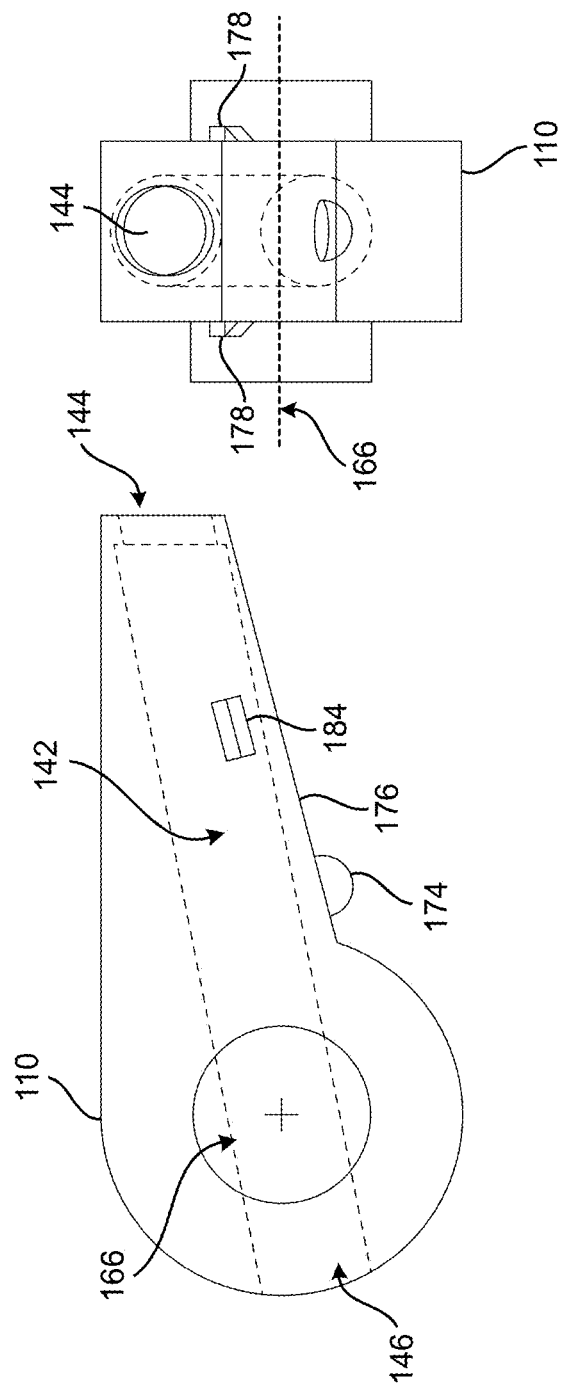

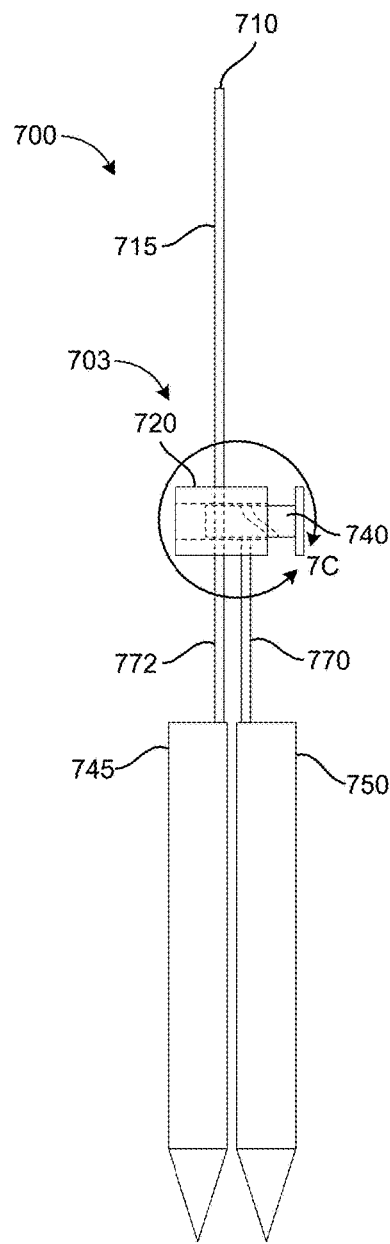
FIG. 7A
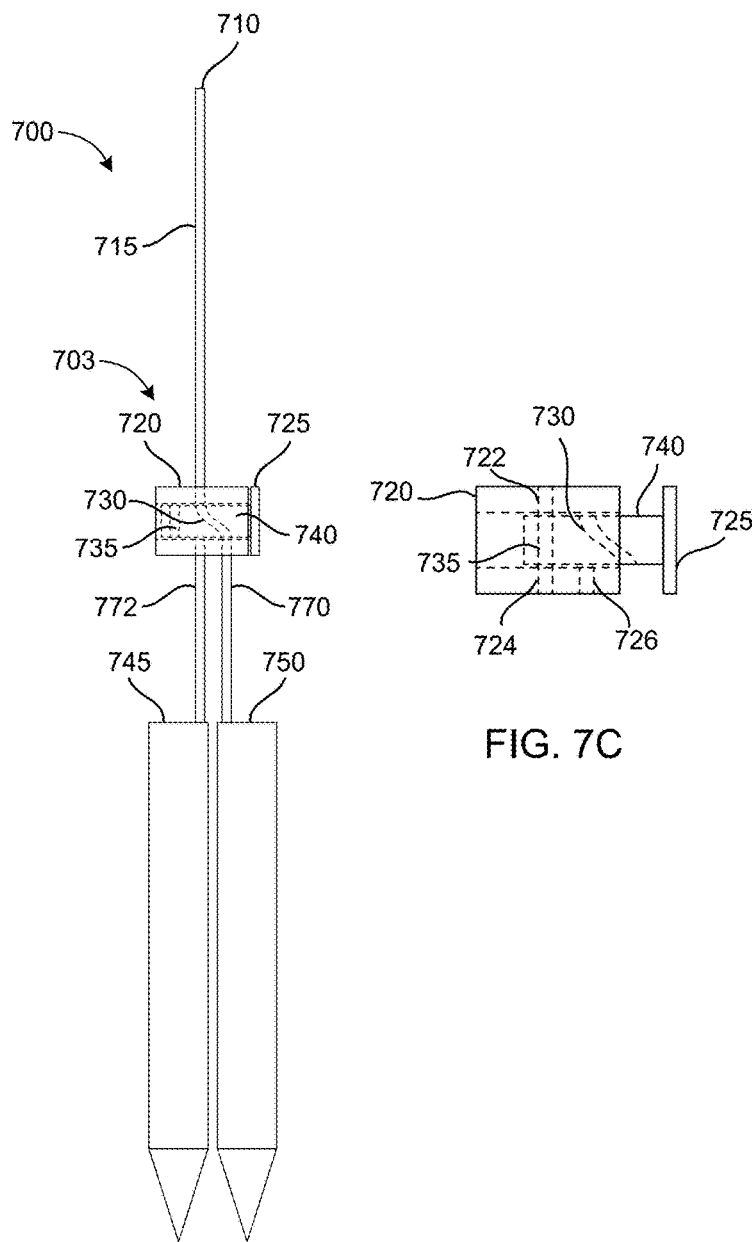
FIG. 7B
FIG. 7C

DEVICE FOR MIDSTREAM SAMPLE COLLECTION FROM A CATHETERIZED SUBJECT AND METHOD AND SYSTEMS FOR USE THEREOF

CROSS REFERENCE TO RELATED APPLICATIONS

This application claims benefit of priority pursuant to 35 U.S.C. § 119(e) of U.S. provisional patent application No. 63/010,491, filed Apr. 15, 2020, and 63/089,510, filed Oct. 8, 2020, which are incorporated herein by reference in their entireties.

FIELD

Disclosed herein are devices, methods, and systems for collecting a bodily liquid via a catheter using one hand, wherein the collected liquid may be substantially free of contaminants. In many embodiments, the disclosed devices and methods may allow for collection of urine sample midstream into a sterilized collection container.

BACKGROUND

Collecting a urine specimen from a subject is often useful in medical diagnostics. Urine may be captured in a cup or via catheterization. Both methods may result in contamination of the sample due to bacteria and other contaminants. For specimen capture via cup, the outer dermis, at and around the urethral opening, may be washed and/or sterilized to minimize contamination. Washing/sterilization is also useful when the subject is catheterized. However, urine samples, even those collected via catheterization, may still be contaminated by contaminants (e.g. bacterial from epithelial cells and secretions) near the urethral opening and/or other contaminated regions of a patient contacted by the urine prior to collection.

Uncontaminated urine specimens from female patients can be particularly difficult to obtain. Female urine specimens are frequently contaminated with vaginal secretions, epithelial cells, and surface bacteria that render results from the sample unreliable or unusable. This is especially true in the pediatric, feeble, elderly and obese patient populations.

Vaginal contamination of a urine sample may be confirmed by identification and/or quantitation of vaginal-derived squamous cells, which are not present in the bladder. In many cases, a collected specimen with more than fifteen squamous cells per high powered field (HPF) may be rejected for one or more particular medical tests.

What is needed is a method of obtaining an uncontaminated urine sample from subjects having a high likelihood of producing a contaminated sample.

BRIEF DESCRIPTION OF THE DRAWINGS

Non-limiting and non-exhaustive embodiments of the disclosure are described herein, including various embodiments of the disclosure illustrated in the figures listed below.

FIG. 1A illustrates one embodiment of the disclosed catheter device in collection or open configuration.

FIG. 1B illustrates the catheter device of FIG. 1A in a waste or closed configuration.

FIG. 4A is a detailed side elevation view of a portion of a flow control valve of the catheter device of FIG. 1A.

FIG. 4B is a detailed end elevation view of the portion of a flow control valve of FIG. 4A.

FIGS. 7A and 7B illustrate an embodiment of a catheter device having a diverter device comprising a valve body and an internal flow control director in an extended configuration (waste mode; FIG. 7A) and depressed configuration (collection mode; FIG. 7B). This embodiment also includes a waste receptacle and a collection receptacle.

FIG. 7C is a detail view of a portion of the catheter device of FIG. 7A taken at line 7C of FIG. 7A.

Figures 2A, 2B:
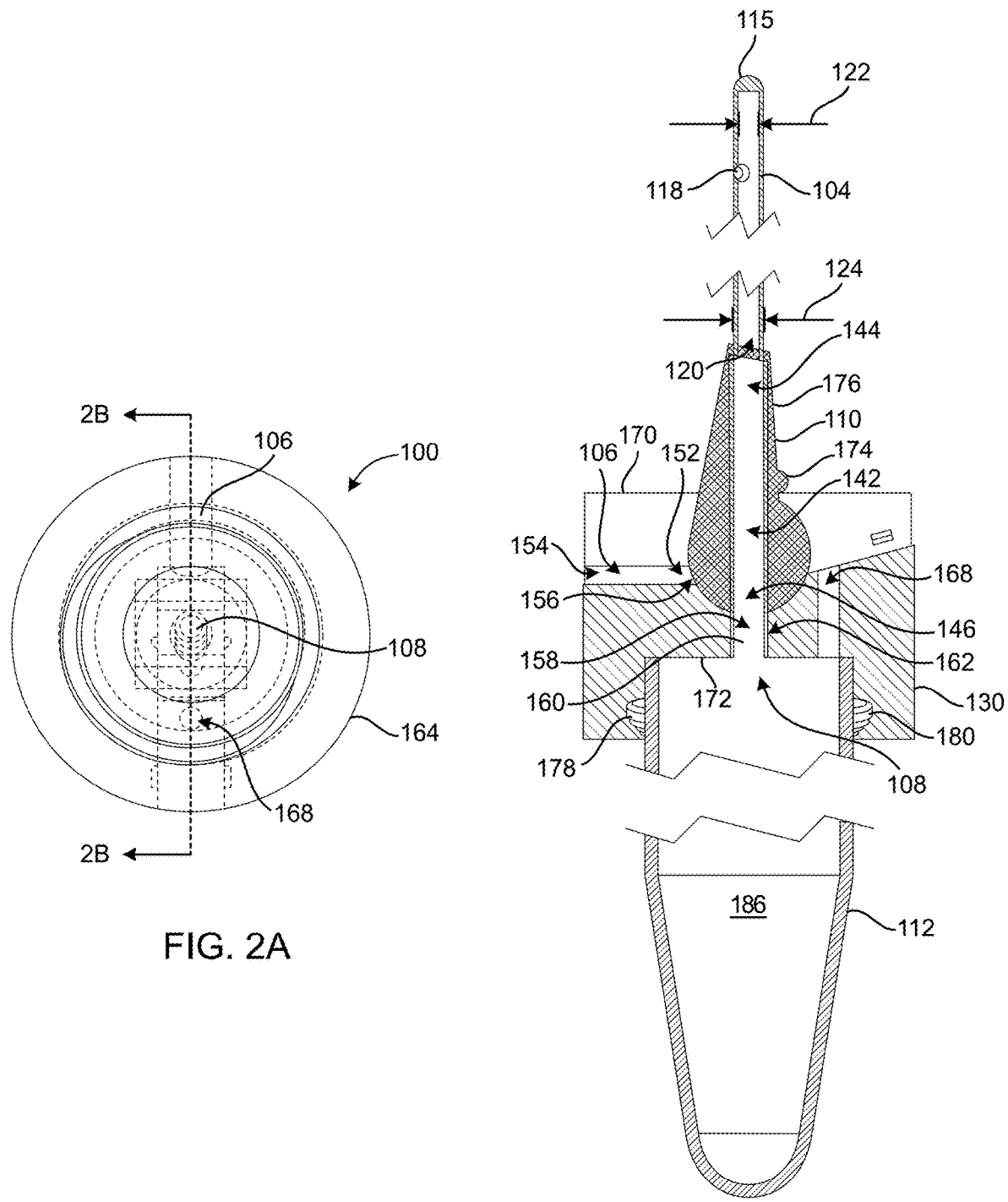
FIG. 2A is a top view of the catheter device of FIG. 1A.
FIG. 2B is a detailed partial section view of the catheter device of FIG. 1A taken along section line 2B-2B of FIG. 2A.

In the following description, numerous specific details are provided for a thorough understanding of the various embodiments disclosed herein. The systems and methods disclosed herein can be practiced without one or more of the specific details, or with other methods, components, materials, etc. In addition, in some cases, well-known structures, materials, or operations may not be shown or described in detail in order to avoid obscuring aspects of the disclosure. Furthermore, the described features, structures, or characteristics may be combined in any suitable manner in one or more alternative embodiments.

DETAILED DESCRIPTION

During catheterization, the initial flow of fluid may carry all or most of the contaminants in the sample. If there are enough contaminants in even a small amount of initial flow, despite the remainder of the sample being free of contamination, the contamination from that small volume of sample may result in the entire sample being unusable. Thus, if this initial flow may be separated and/or discarded before entering the collection receptacle, fewer samples will be rejected.

Disclosed herein are devices and methods for obtaining a sample of bodily fluid 102 from a subject, wherein the sample is substantially free of contamination. The disclosed devices and methods accomplish this by discarding and/or separating the initial flow of fluid, which may be contaminated, from the remainder of the sample thereby allowing the sample to be collected free, or substantially free, of the contamination.

Device

Disclosed herein are devices for collecting a bodily fluid 102, especially urine. In some embodiments, the device is a catheter 100, for example a urinary catheter. The disclosed devices may be used on a variety of human subjects, for example children, adults, males, and females. In some embodiments, the subject may be incapacitated or incapable of aiding in the collection of a urine sample. In many embodiments, the subject is female, and may be overweight or obese.

The disclosed female urethral catheter device includes a fluid conduit 104, a waste channel 106, a collection channel 108, and a fluid diverter 130 positioned between the fluid conduit 104 and the collection channel 108 and waste channel 106. In various embodiments the urethral catheter device 100 may also include a collection receptacle 112 having an internal volume 186. The urethral catheter device 100, and one or more individual components thereof, may be constructed of various natural and/or synthetic materials. In various embodiments the materials may be selected from plastic, rubber, silicone, polyethylene, latex, elastomers, polyurethane and the like.

As shown for example in FIGS. 1A-2B, the fluid conduit comprises a first end 114 and a second end 116. The first end 114 may comprise a first orifice 118 and the second end 116 may define a second orifice 120 fluidly connected to the first orifice 118. The fluid conduit 104 may have an inner diameter 122 and an outer diameter 124. In some embodiments, the outer diameter 124 may be from about 3 Fr to about 36 Fr, wherein a Fr is equal to about 0.33 mm or 0.013 inch. In many embodiments, the outer diameter 124 may be selected based on the characteristics of the subject, for example sex, age, weight, etc. As an example, a medical professional may select a diameter size for an adult female that is about 10 Fr to 12 Fr, while for an adult male the size may be from about 14 Fr to 16 Fr.

The fluid conduit 104 may have a first lumen 126 with an inner diameter of various sizes. In some embodiments the fluid conduit 104 may have a constant inner diameter 122 along its length, that is smaller than, and, in some embodiments, selected based on the outer diameter 124 of the fluid conduit. In many embodiments, the inner diameter 122 may be about 5 Fr to about 10 Fr. The fluid conduit 104 may further include a second lumen 128 with a first end positioned at or near the first end of the fluid conduit 104 and a second end positioned at or near the second end of the fluid conduit 104, wherein the first and second ends of the fluid conduit 104 are in fluid communication, but not with the first lumen 126.

The fluid conduit 104 may be of various lengths. In many embodiments, the medical professional may select the fluid conduit 104 length based on various subject characteristics, such as age, sex, weight, etc. In many embodiments, the fluid conduit 104 length may be from about 12 cm to about 45 cm. As an example, a medical professional may select a fluid conduit 104 for an adult female that is about 15 cm in length, while for an adult male the length of the fluid conduit 104 may be about 40 cm.

Diverter Device

The fluid diverter device 130 may have at least one waste channel 106, a collection channel 108, and a flow control valve 110. The flow control valve 110 may define at least a transfer conduit 142. The transfer conduit 142 may comprise a transfer inlet 144 in fluid communication with the second orifice 120 of the fluid conduit 104 and a transfer outlet 146. In some embodiments, the flow control valve 110 is movable between a first position and a second position. In some embodiments the valve may comprise a waste transfer channel or conduit and a collection transfer conduit.

Flow Control Valve

The flow control valve of the diverter device may be transitioned from a first to a second position and back. In many embodiments, the transition may be due to manual force applied by a medical professional. In some embodiments, the flow control valve may pivot about an axis between a first position 148 and a second position 150. In doing so, the fluid transfer valve 110 may help to re-direct fluid from a waste channel 106 to a collection channel 108, or the collection channel 108 to the waste channel 106. In these embodiments, the flow control valve 110 may comprise a single transfer channel 142. In other embodiments, the flow control valve 110 may comprise a waste transfer channel 106 and collection transfer channel 108, wherein the flow control valve 110 defines a body that may be translated between a first position 148 to a second position 150.

Waste Channel

The waste channel 106 of the fluid diverter 130 may define a first end with a waste inlet 152 and a second end with a waste outlet 154. In some embodiments, the waste channel 106 defines at least one lumen 156 with an inner diameter that is the same or larger than the inner diameter of the fluid conduit.

Collection Channel

The collection channel 108 of the fluid diverter 130 may define a first end with a collection inlet 158 and a second end with a collection outlet 160. In many embodiments, the collection channel 108 may define a lumen 162 with about the same or larger inner diameter than that of the fluid conduit 104. In other embodiments, the lumen 162 of the collection channel 108 may be smaller than the inner diameter of the fluid conduit 104.

Collection Receptacle

The urethral catheter device 100 may further comprise a fluid collection receptacle 112. In many embodiments, the fluid collection receptacle 112 is configured to collect a fluid 102 exiting the collection outlet 160 of the collection channel 108. In some embodiments, the fluid collection receptacle 112 may be a clean and sterile receptacle 112 having a fluid capacity sufficient to hold the volume of a bodily fluid 102 for at least one medical assay. In many embodiments, the receptacle 112 may be of various sizes. In many embodiments, the size, shape, and material of the receptacle 112 is selected based on one or more characteristics of the subject and/or the medical assay.

The collection receptacle 112 may be variously shaped. In some embodiments, the collection receptacle 112 may be a conical tube, for example a 15 ml or 50 ml conical tube. The collection receptacle 112 may engage the diverter device 130 in various ways, for example by press fit, threading, etc. In some embodiments, the diverter device 130 defines a cap structure 164 that may include one or more structures designed to receive, and securely hold, the collection receptacle 112.

In various embodiments, the diverter device 130 may define a cap, lid, or cover 164 for the collection receptacle 112. In these embodiments, the diverter device 130 may be useful in sealing the collection receptacle 112 to maintain integrity of the receptacle, contain the sample, and/or prevent contamination after collection of the sample.

Method

The described catheter device 100 and/or 700 (discussed below) is configured to allow a medical practitioner to insert the device 100 into the urethra and collect a sterile sample with a single hand. In some embodiments, the catheter device 100 or 700 may be sterile. In some embodiments, the medical practitioner may perform the procedure on a female patient as follows: one hand of the practitioner (in some cases, the non-dominant hand) is used to retract the patient's labia—this hand may be referred to as the non-sterile hand;

the other hand (in some cases, the dominant hand) is then used to perform the catheterization procedure—that is insertion of the fluid conduit 104 into the urethra of the patient, allowing an initial volume of fluid 102 to flow through the lumen 126 of the fluid conduit 104 and exit the waste channel outlet 154, and then moving the flow control valve 110 from a first position 148 to a second position 150, wherein the fluid exits the collection channel 108 and enters a collection receptacle 112. Thus, in some cases the disclosed catheter device 100 may be used by a single medical practitioner to catheterize the patient and collect a sample from the patient midstream.

As described above, the fluid diverter device 130 of the catheter device 100 and/or 700 may be manually moved back and forth from a waste setting (e.g., the first position 148) to a collection setting (e.g., the second position 150). In many embodiments, in the waste setting 148, fluid 102 from the subject is directed to a waste receptacle, rag, towel, pad, etc. In some cases, fluid 102 diverted to waste may be collected for analysis, while in other embodiments, the waste fluid 102 is discarded.

The disclosed catheter device 100 and/or 700 may be used to collect urine that is substantially free of contaminants from the subject. In these embodiments, the fluid conduit 104 of the catheter device 100 may be inserted into a body cavity of a subject, next, fluid from the body cavity is allowed to flow through the fluid conduit 108 to the diverter device 130, where it is directed to a waste channel 106; fluid 102 is allowed to flow through the waste channel 106 until an amount sufficient to flush contaminants that may have entered the fluid conduit 104. Next, the flow control valve 110 of the diverter device 130 may be switched to a collection mode (e.g., the second position 150), wherein the fluid 102 is directed into a sterile, clean collection receptacle 112. In these embodiments, the catheter device 100 may remain in the collection mode until an amount of fluid 102 has been captured by the collection receptacle 112.

Subject

The disclosed devices and methods may be useful in collecting a bodily fluid 102 from various subjects/patients. In some embodiments, the subject is a mammal, for example a human male or female subject. In many embodiments the subject is a female human, for example an obese female. In some embodiments, the subject may be an adult or child, for example a child under the age of puberty or legal majority. In some embodiments the patient is elderly, for example 60 years of age or older, especially older than 70 years, 75 years, 80 years, 85 years, 90 years, 95 years, or 100 years. In many embodiments the subject may be elderly, disabled, obese, conscious, unconscious, incapacitated, and/or uncooperative. In many embodiments, an uncooperative patient may be unwilling or incapable of following direction from a medical professional.

Substantially Free of Contamination

The disclosed urethral catheter device 100 and/or 700 may be useful in the capture of a urine specimen that is substantially free of contaminants, such as non-urethral cells, vaginal squamous cells, detritus, and/or microbial cells. In some embodiments, urine samples collected from many patients, especially female patients, may be contaminated by bacteria. In many cases, contaminants may be located at or near the urethral opening and/or other contaminated regions of a patient contacted by the urine prior to collection.

Uncontaminated urine specimens from female patients can be particularly difficult to acquire. Urine specimens are frequently contaminated with vaginal secretions and bacteria that render the sample unusable for an intended medical test or analysis. While urine samples from men can be contaminated as well, the female anatomy complicates the process of obtaining uncontaminated urine samples. When providing a urine sample, especially into a specimen cup, the urine of a female patient may flow over the labia and/or over the vaginal skin before falling free for collection. This often results in vaginal contamination of the specimen.

Contamination of a urine sample can often be identified based on the number of vaginal squamous cells present in the sample. Vaginal squamous cells are not present in the bladder or urethra. In many embodiments, a collected specimen may be deemed contaminated, wherein 15 or more squamous cells appear in a high powered field (HPF). In these embodiments, the sample may be too contaminated for a particular medical test. Samples substantially free of contaminants may have vaginal squamous cell counts less than about 15 cells per high powered field and/or males may have fewer than about two white blood cells (WBCs) per HPF and females fewer than about five WBCs per HPF.

Microscopic Urinalysis

Microscopic examination is an indispensable part of urinalysis; the identification of casts, cells, crystals, and bacteria aids in the diagnosis of a variety of conditions. To prepare a urine specimen for microscopic analysis, a fresh sample of 10 to 15 mL of urine should be centrifuged at 1,500 to 3,000 rpm for five minutes. The supernatant then is decanted and the sediment resuspended in the remaining liquid. A single drop is transferred to a clean glass slide, and a cover slip is applied.

Leukocytes may be seen under low- and high-power magnification. Men normally have fewer than two white blood cells (WBCs) per HPF; women normally have fewer than five WBCs per HPF. Epithelial cells often are present in the urinary sediment. Squamous epithelial cells are large and irregularly shaped, with a small nucleus and fine granular cytoplasm; their presence suggests contamination.

Due to the difficulty in obtaining uncontaminated urine samples (especially from children, elderly or incapacitated, female patients, and in particular obese female patients) a medical practitioner may request a urine sample be collected via catheterization. As noted above, even in these cases the sample is susceptible to contamination. For example, the urethral opening may be contaminated with bacteria or other contaminants that are not removed with routine cleansing. This may lead to the initial stream of urine being contaminated. In many cases, despite the patient lacking a bladder infection, the initial stream of urine may be so contaminated, that the entire sample is contaminated.

After receiving urine analysis results from a contaminated specimen, a medical practitioner may not know whether the contamination originated in the bladder or during insertion of the catheter. Thus, the practitioner must decide whether to: 1) obtain a second sample putting the patient through a second catheterization, 2) begin a course of antibiotics to treat a bacterial infection in the bladder, or 3) disregard the contamination as an artifact of insertion. Each of these decisions comes with risk to the patient. For example, treating the patient with antibiotics may, if the contamination occurred upon insertion, be unnecessary and lead to further antibiotic resistance side effects of antibiotic use such as a yeast infection or diarrhea, such as may be cause by a a *Clotridium difficile* infection, while mistakenly attributing the infection to an artifact may allow a patient to develop a more severe infection and/or additional complications.

As described above, even catheterized urine samples are susceptible to contamination because the urethral opening retains a small plug of mucous and squamous cells, even after standard external cleansing. As the catheter is inserted into the urethral opening, the mucous and squamous cells are forced into the catheter. The initial stream of urine flushes this contamination into the specimen container(s) resulting in a contaminated specimen.

The systems and methods described herein provide for capturing the sample midstream, after liquid has started to flow through the device and flushed the initial contamination. While the systems and methods are applicable to a wide variety of catheterized liquid flows, many of the examples provided herein are described in terms of urine samples from a catheterized urethra. In many cases, the subject being catheterized is unconscious, uncooperative, aged, obese, and/or female.

Collecting a urine specimen midstream allows the medical practitioner to discard and/or separate the initial stream of urine, which may carry the contaminants, for example mucous, vaginal squamous cells, bacteria, etc. The contaminants may then be discharged/discarded and/or directed into a non-sample receptacle for contaminants. During sample collection, an operator (e.g., a medical practitioner) may manually activate the diverter device to redirect fluid traveling through the fluid conduit from a waste channel into a collection channel, and ultimately into a sample receptacle.

EXAMPLES

Example 1

An embodiment of the disclosed device, depicted in FIGS. 1A-6E, is now described. FIG. 1A depicts a device embodiment in an "open" or "collect" mode (e.g., the second position 150). FIG. 1B shows the device 100 in a "closed" or "waste" mode (e.g., the first position 148). In this embodiment, the fluid conduit 104 has a first end 114 and a second end 116, wherein a first orifice 118 and a second orifice 120 may be located, respectively. In this embodiment, the second end 116 of the fluid conduit may be partially obscured by the diverter device 130, which may include a flow control valve 110, a waste channel 106, and a collection channel 105. In this embodiment, the diverter device 130 may define a flow control valve 110 defining a pivot structure 166. In this embodiment the diverter device 130 may also define a cap structure 164. In this embodiment, the fluid conduit 104 is inserted into the transfer channel 142 of the pivot structure 166 or fluid control valve 110. This may aid in securing the fluid conduit 104, and result in the lumen 126, 128 of the fluid conduit 104 near the second end 116 being a transfer channel 142. In other embodiments, the transfer channel 142 and fluid conduit 104 may be separate structures.

In this embodiment, the cap structure 164 may be designed to cap or secure the collection receptacle 112. The cap 164 of the diverter device 130 may further be configured to securely hold the fluid transfer valve 110, allowing the fluid transfer valve 110 to move, rotate, transition, or pivot by a user. This may allow the fluid transfer valve 110 to be moved from a first position 148 to a second position 150, and back. FIG. 6 is another embodiment of the disclosed cap 164'.

In the embodiment of FIG. 1B, the first position 148 is shown, where the closed or waste mode is depicted. In this mode, the second orifice 120 of the fluid conduit 104 is in fluid communication with the waste channel 106 of the diverter device 130. In this mode, fluid 102 entering the first orifice 118 of the fluid conduit 104 may traverse the fluid conduit 104 and exit at the second orifice 120 of the fluid conduit 104. After leaving the second orifice 120 of the fluid conduit 104, the fluid 102 may enter the transfer channel 142 of the fluid control valve 110 or enter the waste channel 106 of the diverter device 130.

In some further embodiments a waste collection receptacle may be attached or otherwise positioned for accepting and capturing fluid 102 exiting the waste channel 106. In the embodiment shown in FIG. 1A, fluid 102 may exit the waste channel 106 of the diverter device 130 at the waste channel outlet 154 to be captured or discarded.

In the second position 150, here shown for example in FIG. 1A, the device 100 is in the open or collection mode. In this mode, the second orifice 120 of the fluid conduit 104 (or transfer channel 142 of the fluid control valve 110) is in fluid communication with the collection channel 108 of the diverter device 130. In this mode, fluid 102 entering the first orifice 118, at the first end 114 of the fluid conduit may traverse the fluid conduit 104, via the first lumen 126, and exit at the second orifice 120 of the fluid conduit 104. The fluid 102 may then enter the transfer channel 142 of the fluid control valve 110, or may enter the collection channel 108 of the diverter device 130. The fluid 102 may then exit the collection channel 108 and be captured in the collection receptacle 112.

FIG. 2B is a cross sectional view of the device along section line 2B-2B of FIG. 2A, wherein the device 100 is in the open or collection mode (e.g., the second position 150), and the diverter device 130 is in the second position 150. This view shows that the first end 114 of the fluid conduit 104 ends at a tip 115, which, in this embodiment, is rounded and sealed, while the first orifice 118 is defined at a side of the fluid conduit 104. This may allow for easier application of the urethral device 100 with less discomfort for the subject. In these embodiments, a plurality of first orifices 118 may be positioned about the sides of the fluid conduit 104 near the first end 114, wherein the plurality of first orifices 118 are in fluid communication with the lumen 126, 128 of the fluid conduit 104.

As shown in FIG. 2B, the cap 164 may define a vent structure 168 that traverses the cap 164 to fluidly connect the top 170 of the cap 164 to the internal volume 186 of the fluid receptacle 112. The vent structure 168 may be open to the environment (e.g., when the diverter device 130 is in collection mode (e.g., the second position)). For example, the vent structure 168 may include a conduit that passes between the top 170 and the bottom 172 of the cap 164, which is in fluid communication with the interior of the collection receptacle 142. In these embodiments, the vent 168 may allow for air to escape from the collection receptacle 142 as a volume of fluid 102 enters the receptacle 112 and displaces a similar volume of air. In some embodiments, the vent 168 may include a filter to prevent environmental air from entering the sterile environment of the collection receptacle 142.

The vent 168 may be configured to accept a sealing structure 174 such as a detent, tab, pin, or other structure to seal the vent 168. In this embodiment, the detent 174 is positioned on a surface such as a lower surface 176 of the fluid control valve 110, and configured to engage and partially, or completely, insert into the vent 168 of the cap 164. This may help to affect a seal of the vent 168 when the diverter device 130 is in a closed mode (e.g., the first position 148). In this view accepting threads 178 may be seen in the cap 164. The accepting threads 178 may aid in securing the collection receptacle 142, which may be configured with engaging threads 180 near an end of the collection receptacle 142.

Figure 3C:
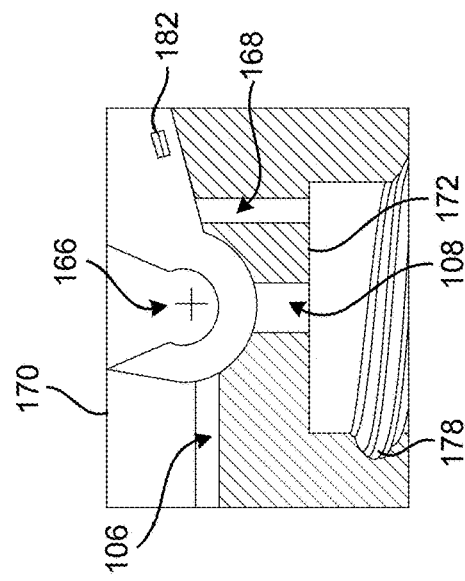
FIG. 3C is a section view of the cap of FIG. 3A taken along section line 3C-3C of FIG. 3B
Figure 3B:
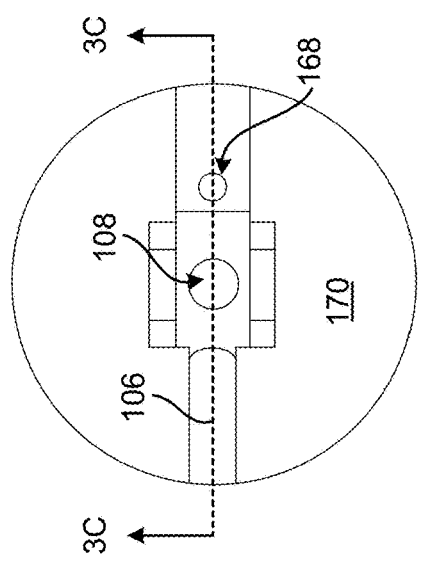
FIG. 3B is a top plan view of the cap of FIG. 3A.
Figure 3A:
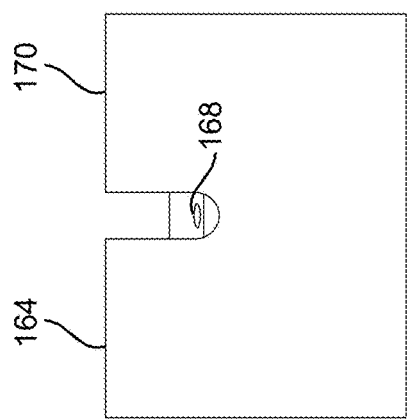
FIG. 3A is a side elevation view of a cap of the catheter device of FIG. 1A.

FIGS. 3A-3C are detailed, cross-sectional views of the cap structure 164, without the diverter device 130 in place. This view shows a pivot center 166 for the diverter structure ("+") and a locking structure 182, which may be configured to interact with a corresponding structure 184 on the pivot of the diverter device 130. The locking structure 182 and corresponding structure 184 may help to securely hold the pivot 166 in the first position 148, which may aid in maintaining a seal of the vent 168. FIG. 3C shows a view of a channel that allows for movement of the pivot inside the cap.

FIGS. 4A-4B are detailed views of the pivot structure 166. In this view the pivot is shown from the side, and front, which shows the channel 142 adapted to accept the fluid conduit 104.

Figure 5A:
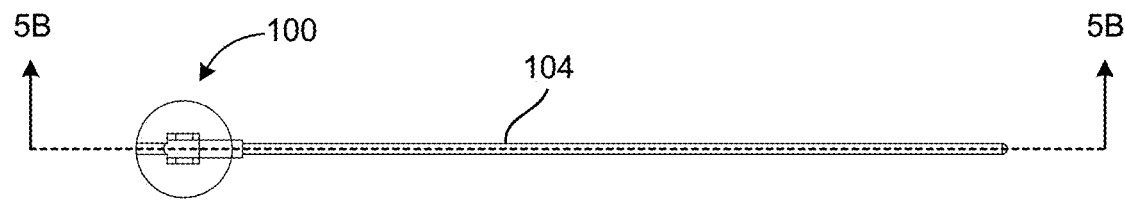
FIG. 5A is a top plan view of the catheter device of FIG. 1A, in a closed configuration.
Figure 5B:
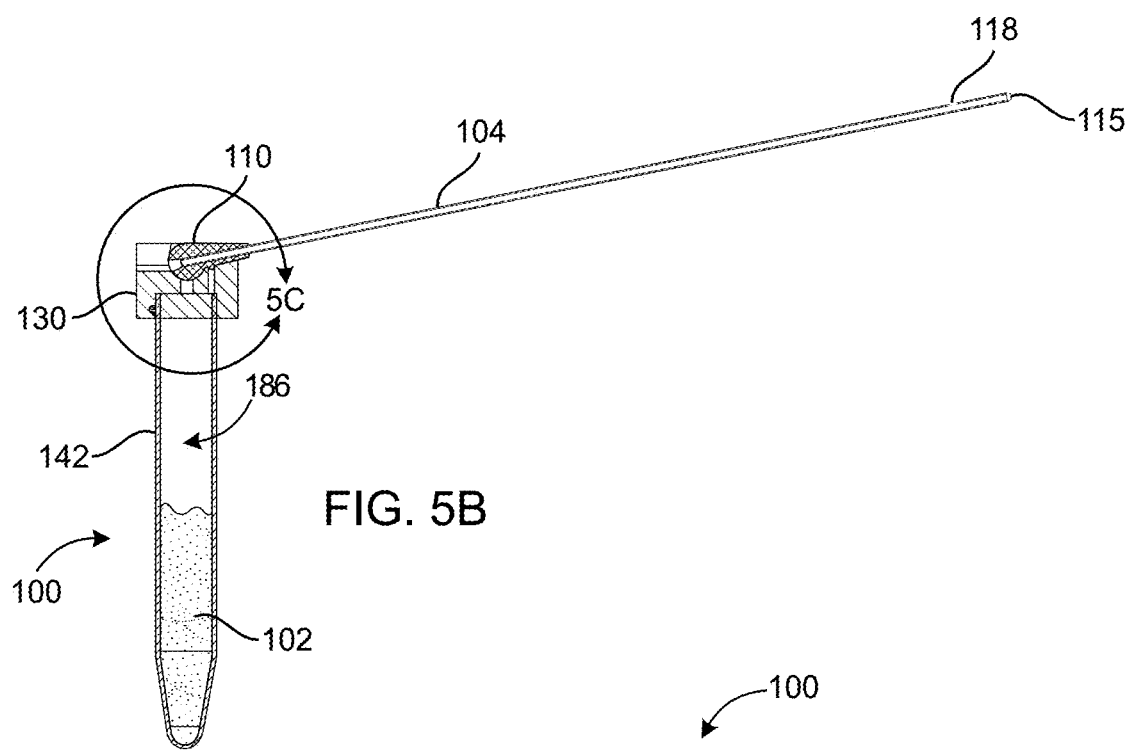
FIG. 5B is a section view of the catheter device of FIG. 1A in a closed configuration, taken along section line 5B-5B of FIG. 5A.
Figure 5C:
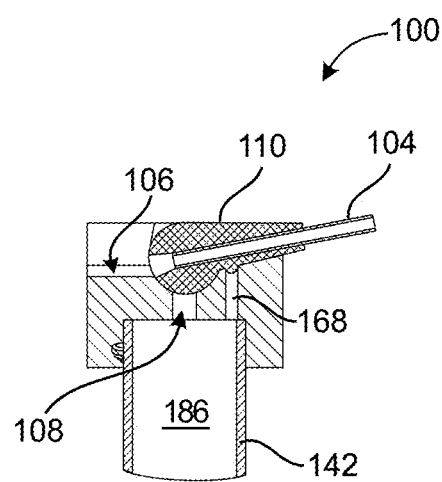
FIG. 5C is a detail view of the a portion of the catheter device of FIG. 1A taken at line 5C of FIG. 5B.
Figure 6A:
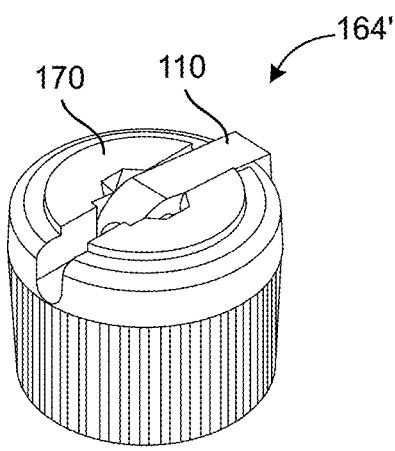
FIG. 6A shows an isometric view of an embodiment of a cap suitable for use with the catheter device of FIG. 1A.
Figure 6D:
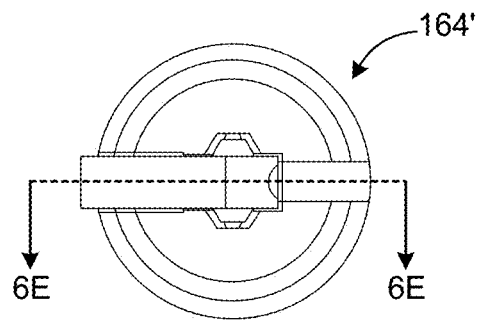
FIG. 6D shows a top plan view of the cap of FIG. 6A.
Figure 6B:
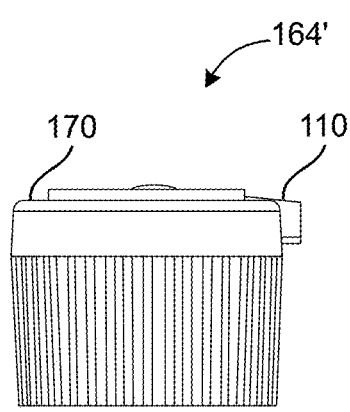
FIG. 6B shows a side elevation view of the cap of FIG. 6A.
Figure 6E:
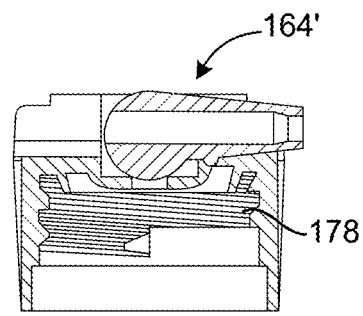
FIG. 6E shows a cross section view of the cap of FIG. 6A taken along line 6E-6E of FIG. 6D.
Figure 6C:
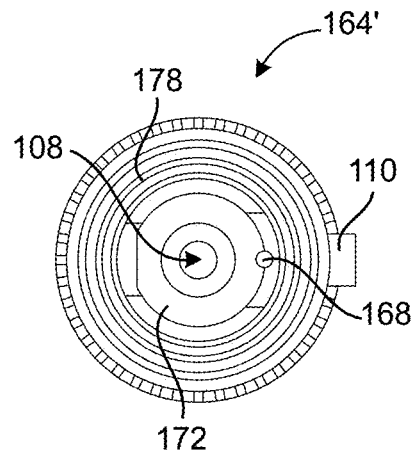
FIG. 6C shows a bottom plan view of the cap of FIG. 6A.

FIGS. 5A-5C are views of the device 100, similar to that shown in FIG. 1A, wherein the diverter device 130 is in the closed or waste mode (e.g., the first position 148). In this position, urine may exit the waste channel 106, which may be positioned at the side of the cap 164 of the diverter device 130.

Example 2

FIGS. 7A-7B illustrate an embodiment of a catheter device 700 with a manually operable diverter device 703, comprising a diverter valve body 720, and a flow director body 740. The diverter valve body 720 may comprise a transfer channel 722, a waste channel 724, and a collection channel 726 of the diverter device 703. The transfer channel 722 may be configured to be in fluid communication with a fluid conduit 715, wherein the fluid conduit 715 is suitable for collecting a fluid sample from a subject, as described with respect to the fluid conduit 104, and passing the fluid to the transfer channel 722. The transfer channel 722 directs fluid from the fluid conduit 715 to the flow director body 740. The transfer channel 722 may direct fluid to one or more channels within the flow director body 740 (e.g., a waste channel 735 and/or a collection channel 730). The flow director body 740 directs fluid to one of the collection channel 726 or the waste channel 724 of the diverter valve body 720. In this embodiment, the flow director body 740 includes a waste channel 735 and a collection channel 730 therein which are not in fluid communication with one another, for example to prevent or reduce contamination of a urine specimen. The flow director body 740 may include an operator 725 suitable to enable a user to move the flow director body 740 between the first position and the second position. In the example shown, the operator 725 is a planar button suitable to be grasped or pushed by a user's fingers. Other suitable operators 725 may be used.

The embodiment of FIGS. 7A and 7B show a diverter device 703 with a flow director body 740 positionable in a diverter valve body 720 between a first position (see, e.g., FIG. 7A and in greater detail in FIG. 7C) in the diverter valve body 720 and a second position in the diverter valve body 720, shown for example in FIG. 7B. The second position may be when the flow director body 740 is inserted or depressed into the diverter valve body 720 of the diverter device 703. In the first position, the flow director body 740 is partially inserted into the diverter valve body 720 and the waste channel 735 fluidly connects the fluid conduit 715 (optionally via an inlet of the transfer channel 722) with a waste receptacle 745 e.g., via the waste channel 724 of the diverter valve body 720. In these embodiments, a waste conduit 772, is positioned between the diverter valve body 720 of the diverter device 703 and the waste receptacle 745, thereby completing a fluid connection with the fluid conduit 715 and the waste receptacle 745. In other embodiments, the first and second positions may be opposite, such that in the first position, fluid is directed into a collection receptacle 750 and/or the flow director body 740 is at least partially (e.g., fully) inserted into the diverter valve body 720 of the diverter device 703.

FIG. 7B illustrates the embodiment of the catheter device 700 wherein the flow director body 740 is fully depressed and the fluid conduit 715 is in fluid communication with a collection receptacle 750. Here, the flow director body 740 is in the second position is at least partially inserted (e.g., fully inserted or more inserted that the first position) into the diverter valve body 720. In this position, the collection channel 730 of the flow director body 740 connects the fluid conduit 715 (optionally via the transfer channel 722) with a collection receptacle 750 e.g., via the collection conduit 726 of the diverter valve body 720. In these embodiments, a collection conduit 770, may be positioned between the diverter valve body 720 and the collection receptacle 750 completing a fluid connection between the fluid conduit 715 and the collection receptacle 750.

FIGS. 7A and 7B show a diverter device 703 wherein the waste transfer channel 735 of the flow director body 740 is substantially linear, whereas the collection transfer channel 730 is curvilinear. In other embodiments, the two channels 735, 740 may be variously configured (linear, curved, angled, etc.) to achieve the ability to capture a sample in mid-stream.

It is appreciated that any of a wide variety of variations, shapes, configurations, modifications, combinations, and permutations of the various elements could be made. The above description provides numerous specific details for a thorough understanding of the embodiments described herein. However, those of skill in the art will recognize that one or more of the specific details may be omitted, modified, and/or replaced by a similar process or system.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

We claim:

1. A urethral catheter device comprising:
   a fluid conduit having
      a first end defining a first orifice configured for insertion into a urethra of a patient; and
      a second end defining a second orifice in fluid communication with the first orifice;
   a fluid diverter device having at least
      a waste channel having a first end with a waste inlet and a second end with a waste outlet;
      a collection channel having a first end with a collection inlet and a second end with a collection outlet; and a flow control valve defining a transfer conduit having a single transfer inlet in fluid communication with the second orifice of the fluid conduit and a transfer outlet, wherein the flow control valve is movable between a first position and a second position; and a fluid collection receptacle configured for removable connection with the collection outlet; wherein in the first position, the transfer outlet of the fluid diverter device is in fluid communication with the waste inlet to conduct fluid entering the first orifice of the fluid conduit into the waste channel to discharge an initial volume of urine contaminated during insertion of the fluid conduit into the urethra; and in the second position, the transfer outlet of the fluid diverter device is in fluid communication with the collection inlet to conduct fluid entering the first orifice of the fluid conduit through the collection channel and into the fluid collection receptacle.

2. The urethral catheter device of claim 1, wherein the diverter device securely holds the fluid conduit and allows the fluid conduit to pivot as the flow control valve moves between the first position and the second position.

3. The urethral catheter device of claim 1, further comprising a waste receptacle configured for removable connection with the waste outlet, wherein when
the fluid diverter device is in the first position, the second orifice of the fluid conduit is fluidly connected to the waste receptacle.

4. A method for using the urethral catheter device of claim 1, comprising:
grasping the urethral catheter device with one hand;
revealing a urethral opening of a patient with another hand;
inserting the fluid conduit of the urethral catheter device into the urethral opening; and
and allowing a fluid to enter the fluid conduit of the urethral catheter device.

5. The method of claim 4, wherein the patient is female.

6. The method of claim 5, wherein the patient is one or more of pre-pubescent, aged, incapacitated, obese, and unresponsive.

7. The method of claim 6, wherein the one hand is sterile.

8. The urethral catheter device of claim 1, wherein the fluid conduit is moveable between the first position and the second position.

9. The urethral catheter device of claim 8, the waste receptacle in fluid communication with the waste channel.

10. A method for using the urethral catheter device of claim 2, comprising:
grasping the urethral catheter device with one hand;
revealing a urethral opening of a patient with another hand;
inserting the fluid conduit of the urethral catheter device into the urethral opening; and
allowing a fluid to enter the fluid conduit of the urethral catheter device.

11. The method of claim 10, wherein the patient is female.

12. The method of claim 11, wherein the patient is one or more of pre-pubescent, aged, incapacitated, obese, and unresponsive.

13. The method of claim 12, wherein the one hand is sterile.

14. A method for using the urethral catheter device of claim 3, comprising:
grasping the urethral catheter device with one hand;
revealing a urethral opening of a patient with another hand;
inserting the fluid conduit of the urethral catheter device into the urethral opening; and
allowing a fluid to enter the fluid conduit of the urethral catheter device.

15. The method of claim 14, wherein the patient is female.

16. The method of claim 15, wherein the patient is one or more of pre-pubescent, aged, incapacitated, obese, and unresponsive.

17. The method of claim 16, wherein the one hand is sterile.

18. A method for using the urethral catheter device, comprising:
grasping the urethral catheter device with one hand, wherein the device comprises;
a fluid conduit having
a first end defining a first orifice configured for insertion into a urethra of a patient; and
a second end defining a second orifice in fluid communication with the first orifice;
a fluid diverter device having at least
a waste channel having a first end with a waste inlet and a second end with a waste outlet;
a collection channel having a first end with a collection inlet and second end with a collection outlet; and
a flow control valve defining a single transfer conduit having a transfer inlet in fluid communication with the second orifice of the fluid conduit and a transfer outlet, wherein the flow control valve is movable between a first position and a second position; and
a fluid collection receptacle configured for removable connection with the collection outlet; wherein
in the first position, the transfer outlet of the fluid diverter device is in fluid communication with the waste inlet to conduct fluid entering the first orifice of the fluid conduit into the waste channel to discharge an initial volume of urine contaminated during insertion of the fluid conduit into the urethra; and
in the second position, the transfer outlet of the fluid diverter device is in fluid communication with the collection inlet to conduct fluid entering the first orifice of the fluid conduit through the collection channel and into the fluid collection receptacle;
revealing a urethral opening of a patient with another hand;
inserting the fluid conduit of the urethral catheter device into the urethral opening; and
and allowing a fluid to enter the fluid conduit of the urethral catheter device.

19. The method of claim 18, wherein the patient is one or more of female, pre-pubescent, aged, incapacitated, obese, and unresponsive.

20. The method of claim 19, wherein the one hand is sterile.

21. The method of claim 20, wherein the diverter device securely holds the fluid conduit and allows the fluid conduit to pivot as the flow control valve moves between the first position and the second position.

* * * * *